(12) United States Patent  
Grodzins

(10) Patent No.: US 6,542,574 B2
(45) Date of Patent: Apr. 1, 2003

(54) SYSTEM FOR INSPECTING THE CONTENTS OF A CONTAINER

(75) Inventor: Lee Grodzins, Lexington, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 10/101,671

(22) Filed: Mar. 20, 2002

(65) Prior Publication Data

US 2002/0097836 A1 Jul. 25, 2002

Related U.S. Application Data

(62) Division of application No. 09/599,386, filed on Jun. 22, 2000, which is a continuation-in-part of application No. 09/395,331, filed on Sep. 13, 1999, now Pat. No. 6,249,567, said application No. 09/599,386, filed on Jun. 22, 2000.
(60) Provisional application No. 60/110,525, filed on Dec. 1, 1998, and provisional application No. 60/140,767, filed on Jun. 24, 1999.

(51) Int. Cl.⁷ .............................................. G01N 23/04
(52) U.S. Cl. ........................................ 378/57; 378/137
(58) Field of Search ............................ 378/57, 86–90, 378/137

(56) References Cited

U.S. PATENT DOCUMENTS

| 3,955,089 A | 5/1976 | McIntyre et al. ............ 350/399 |
| 4,002,917 A | 1/1977 | Mayo ..................... 250/445 T |
| 4,144,457 A | 3/1979 | Albert .................... 250/445 T |
| 4,149,076 A | 4/1979 | Albert ....................... 250/402 |
| 4,194,123 A | 3/1980 | Wittry ..................... 250/492 A |
| 4,196,351 A | 4/1980 | Albert .................... 250/416 TV |
| 4,535,243 A | 8/1985 | Peschmann .............. 250/363 S |
| 4,566,113 A * | 1/1986 | Donges et al. ................ 378/57 |
| 4,598,415 A | 7/1986 | Luccio et al. ............... 378/119 |
| 4,672,615 A | 6/1987 | Kelly et al. ..................... 372/2 |
| 4,694,457 A | 9/1987 | Kelly et al. ..................... 372/2 |
| 4,730,350 A | 3/1988 | Albert ......................... 378/10 |
| 4,864,142 A | 9/1989 | Gomberg .............. 250/390.04 |
| 5,022,062 A | 6/1991 | Annis .......................... 378/86 |
| 5,097,492 A | 3/1992 | Baker et al. .................. 378/22 |
| 5,153,900 A | 10/1992 | Nomikos et al. ............. 378/65 |
| 5,237,598 A | 8/1993 | Albert ......................... 378/99 |
| 5,247,561 A | 9/1993 | Kotowski .................... 378/87 |
| 5,442,678 A | 8/1995 | Dinsmore et al. .......... 378/137 |
| 5,504,796 A | 4/1996 | Da Silveira et al. ........ 378/121 |
| 5,548,630 A | 8/1996 | Hell et al. .................. 378/137 |
| 5,682,412 A | 10/1997 | Skillicorn et al. ............ 378/98 |
| 5,684,851 A | 11/1997 | Kurbatov et al. ............. 378/87 |
| 5,696,806 A * | 12/1997 | Grodzins ..................... 378/86 |
| 5,712,889 A | 1/1998 | Lanzara et al. ............... 378/19 |
| 5,841,831 A | 11/1998 | Hell et al. .................... 378/19 |

FOREIGN PATENT DOCUMENTS

DE 197 10 222 A1 9/1998

* cited by examiner

Primary Examiner—Craig E. Church

(57) ABSTRACT

A system for inspecting the contents of a container is provided. The system includes a first source for emitting sequential beams of penetrating electromagnetic radiation from a target in a first set of substantially parallel directions, a conveyor for moving the container relative to the first source, a first detector for detecting the penetrating radiation after interaction with the contents of the container and generating a first set of signals corresponding to each of the substantially parallel directions and a controller for characterizing the contents of the container based at least on the first set of signals. The first detector may be a scatter detector. Similarly, the first detector may be a transmission detector.

11 Claims, 8 Drawing Sheets

SYSTEM FOR INSPECTING THE CONTENTS OF A CONTAINER

This application is a Division of co-pending application Ser. No. 09/599,386, filed Jun. 22, 2000, which is a Continuation-in-Part of application Ser. No. 09/395,331, filed Sep. 13, 1999 now U.S. Pat. No. 6,249,567 (claiming priority from provisional application No. 60/110,525, filed Dec. 1, 1998). Application Ser. No. 09/599,386 further claims priority from provisional application No. 60/140,767, filed Jun. 24, 1999. All of these applications are incorporated herein by reference.

TECHNICAL FIELD

The present invention relates to the production of sequential beams of penetrating electromagnetic radiation and, in particular, to the generation of sequential and parallel beams of radiation in the x-ray region of the electromagnetic wave spectrum.

BACKGROUND TO THE INVENTION

For many applications of x-ray radiation, steerability of the x-ray illumination is advantageous. Methods currently employed for providing a beam that either scans periodically or may be directed to a specified direction are typically massive and slow. This is because current methods attempt to steer the x-ray radiation either by moving the source in its entirety, or by physically moving massive collimators interposed in the path of the x-ray beam. Mechanical scanning systems use x-ray tubes in which the electron beam trajectory is fixed. Consequently, the areas that may be scanned at a given time are limited by how fast the device which steers the x-ray beam can be moved. Further, lead is usually used to absorb any radiation that is undesirable, which makes current x-ray steering devices heavy and awkward.

Additionally, with fixed electron beam sources, x-ray imaging may be distorted. This is because the x-ray beams pass through an inspected region at different angles thereby subtending different volumes of the inspected object. Mechanical chopper systems with fixed beam size also have a fixed spatial resolution at a fixed distance from the x-ray generator so zooming, or magnification of the image of a particular region of an inspected object, can only be accomplished by manipulating the image pixels.

SUMMARY OF THE INVENTION

In accordance with one aspect of the invention, in a preferred embodiment, an apparatus for generating sequential beams of penetrating electromagnetic radiation is provided. The apparatus includes a source for producing a beam of charged particles and a target. An electromagnetic steering device directs the charged particles to strike the target at a substantially ninety degree angle. The target receives the beam of charged particles and, consequently, emits electromagnetic waves. The electromagnetic waves pass through a collimator and emerge from the array of transmitting regions in a series of parallel beams of electromagnetic radiation as the beam of charged particles is directed at a plurality of specified locations on the target.

In accordance with another aspect of the invention, an apparatus for generating penetrating electromagnetic radiation of variable beam opening is provided. The apparatus has a source for producing a beam of charged particles, a target, and at least one collimator that is moveable in a direction normal to the target in such a manner as to change the spatial resolution.

In accordance with further embodiments of the apparatus, the collimator includes apertures in an absorbing matrix. The absorbing matrix may be lead or mercury. In another embodiment, the collimator includes substantially parallel transmitting rods in an absorbing matrix.

In other preferred embodiments, the source for producing a beam of charged particles includes an electron gun or an ion beam gun. The source for producing a beam of charged particles may also be a cathode ray tube. The charged particles may also be accelerated toward the target such that they attain relativistic energy.

In accordance with another aspect of the invention, a method for generating sequential beams of penetrating radiation is provided in which a source for producing charged particles supplies a beam of particles which is directed to a plurality of specified locations on a target. The charged particles are steered such that they hit the target at a substantially ninety degree angle, and radiation is produced which is then collimated. In a preferred embodiment, the position of the collimator with respect to the source of radiation can be varied such as to change the spatial resolution of the beams and thus produce a true zooming effect.

In accordance with a further aspect of the invention, an improvement is provided to a system of the kind employing penetrating radiation for characterizing an object concealed by a concealing surface. The improvement has an apparatus for generating sequential beams of penetrating radiation. The apparatus includes a source for producing a beam of charged particles, a target, a electromagnetic steering device to force the charged particles to strike the target at a substantially ninety degree angle, and a collimator having an array of transmitting regions disposed near the target. Electromagnetic waves emitted from the target pass through the collimator and emerge from the array of transmitting regions in a series of parallel beams as the beam of charged particles is directed at a plurality of specified locations on the target. The penetrating radiation may also be multiplexed to provide a seamless image.

In accordance with yet a further aspect of the invention, an improvement is provided to a system of the kind employing penetrating radiation for characterizing an object concealed by a concealing surface. The improvement has an apparatus for generating penetrating radiation of variable beam opening. The apparatus includes a source for producing a beam of charged particles, a target, an electromagnetic beam director, and at least one collimator that is moveable in a direction normal to the target in such a manner as to change the spatial resolution.

In accordance with another preferred embodiment of the invention, a method is provided for varying spatial resolution of an imaging system wherein a source for producing charged particles and a collimator are provided, the particles are directed to a plurality of specified locations on a target to produce penetrating electromagnetic radiation, and a distance between the target and the collimator is adjusted. The electromagnetic radiation may also be multiplexed to provide a seamless image.

In accordance with another embodiment of the invention, a system is provided for inspecting the contents of containers which includes a first source for emitting a beam of penetrating electromagnetic radiation from an addressable position on a target in a first direction, a conveyor for moving the container relative to the first source, a second source for emitting penetrating radiation in a direction substantially opposite to the first direction, a first detector for detecting radiation emitted by the first source and generating a first signal, a second detector for detecting radiation emitted by the second source and generating a second signal, and a controller for characterizing the contents of the container based at least on the first and second signals.

BRIEF DESCRIPTION OF THE FIGURES

The foregoing features of the invention will be more readily understood by reference to the following detailed description taken with the accompanying drawings in which:

FIGS. 5(a)–5(c) provide a schematic representation of another preferred embodiment of the present invention wherein a two dimensional array of sequential penetrating radiation is generated and wherein:

FIG. 5(a) provides a top view of the embodiment of the invention.

FIG. 5(b) provides a side view of the embodiment of the invention.

FIG. 5(c) provides a front view of the embodiment of the invention.

DETAILED DESCRIPTION OF SPECIFIC EMBODIMENTS

Figure 1A:
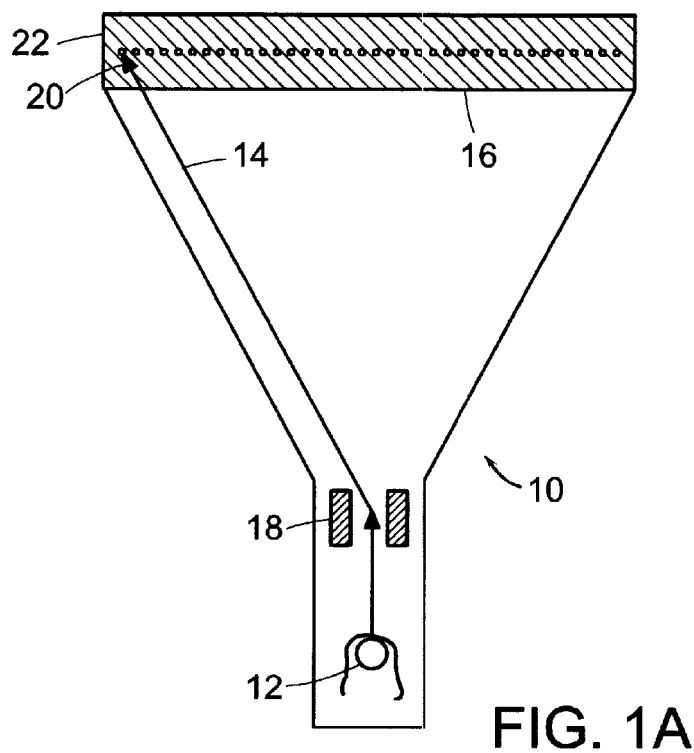
FIG. 1(a) provides a schematic representation in plan view of a source of sequential and x-ray beams in accordance with a preferred embodiment of the present invention.
Figure 1B:
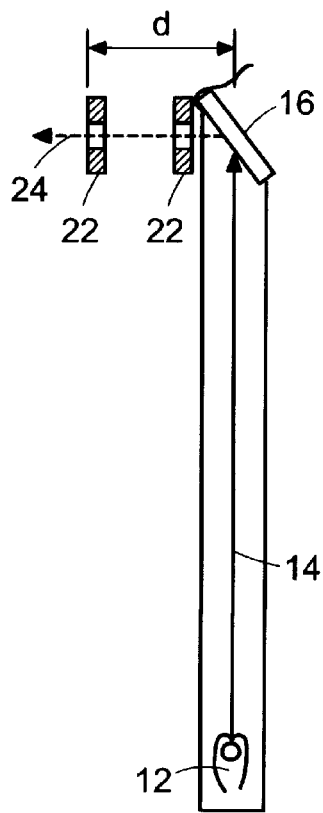
FIG. 1(b) is side view of the embodiment represented by FIG. 1(a).

FIG. 1 (a) shows a plan view of a preferred embodiment of an apparatus for generating sequential beams of penetrating electromagnetic radiation, designated generally by numeral 10. A source 12 supplies a beam of charged particles 14 that are accelerated to a surface of a target 16. The beam 14 can either be scanned across the target 16 in a fixed pattern or directed to successive locations in a particular pattern on the target. A region 20 of the target 16, shown more clearly in FIG. 7, impinged upon by the charged particle beam 14 shall be referred to as the "focal spot size." Electromagnetic beam director 18 can be any electromagnetic beam directing arrangement such as magnetic or electrostatic yokes. Penetrating electromagnetic radiation is emitted by target 16. Penetrating electromagnetic radiation refers to electromagnetic waves of sufficient energy to pass through articles to be inspected, and may be referred to herein, without limitation, as x-rays. The x-rays pass through a collimator 22 disposed a specified distance d, shown more clearly in FIG. 1(b), from the target, thus producing sequential parallel beams of radiation 24.

The region 20 of the target 16 that emits x-rays can be adjusted by focusing or de-focusing the charged particle beam 14 onto the target 16. Collimator 22 is typically displaced 3–10 inches from the target, however, the displacement may be any distance suited to a particular application within the scope of the invention and the displacement may be varied, as will be explained in more detail with respect to FIGS. 6(a) and 6(b) below. Source 12 may be any device which generates charged particles such as a cathode, an electron gun, or an ion beam gun.

Figure 8:
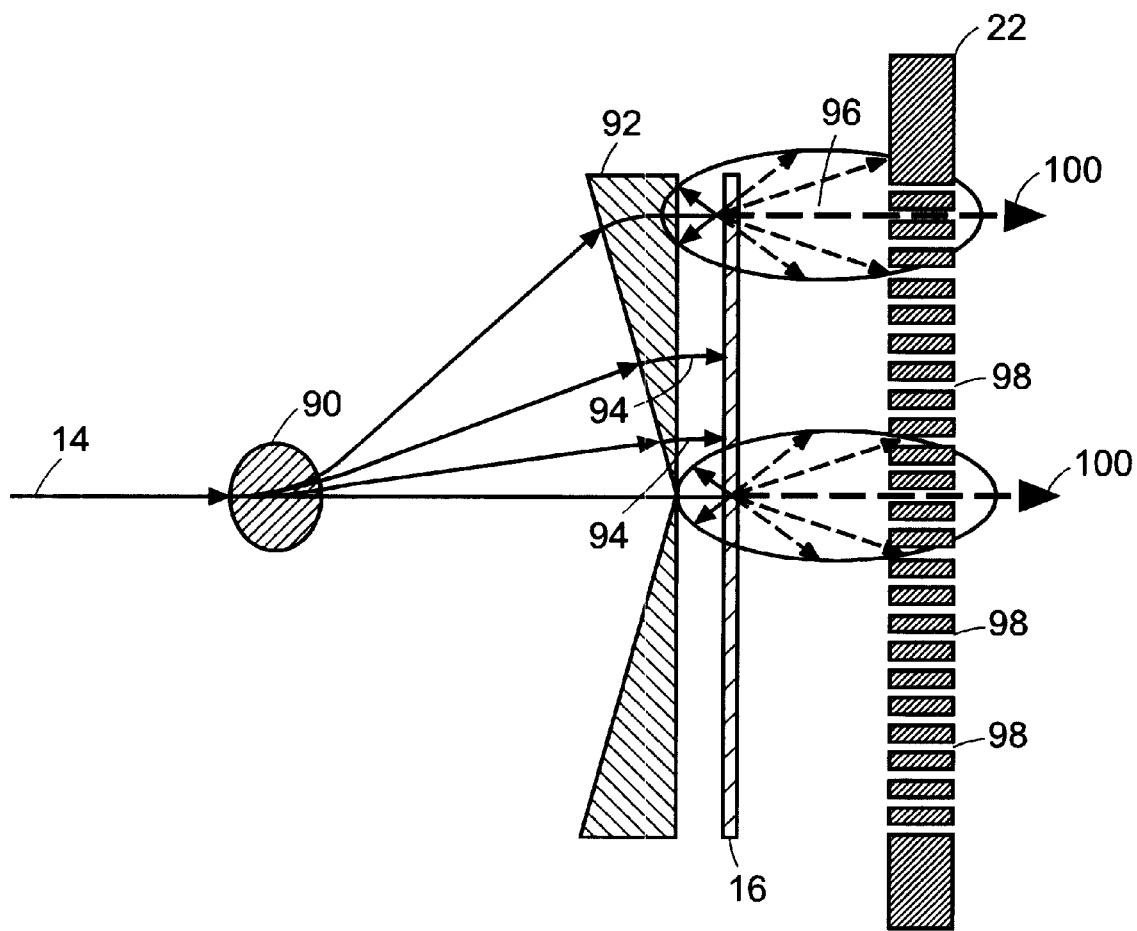
FIG. 8 provides a schematic representation of another preferred embodiment of the present invention wherein uniform high energy electromagnetic radiation is generated.

The beam of charged particles 14 may additionally be steered toward the target 16 by a permanent magnet, an electromagnet, or other steering device 92 as shown in FIG. 8. The target 16 may be made of any material known to produce electromagnetic radiation when charged particles collide with it, such as a metallic anode. The collimator 22 may be made of any material absorptive of electromagnetic radiation, such as lead or mercury. It should also be understood that the collimator 22 can have several independent linear arrays of apertures of different sizes and different configurations. Each array can be activated by moving the collimator plate so that the selected linear array is positioned in front of the target being scanned by the linearly scanned particle beam or by steering the charged particle beam 14 to a new scanning trajectory on the x-ray generating anode; the new trajectory being aligned to another array of apertures.

Figure 2:
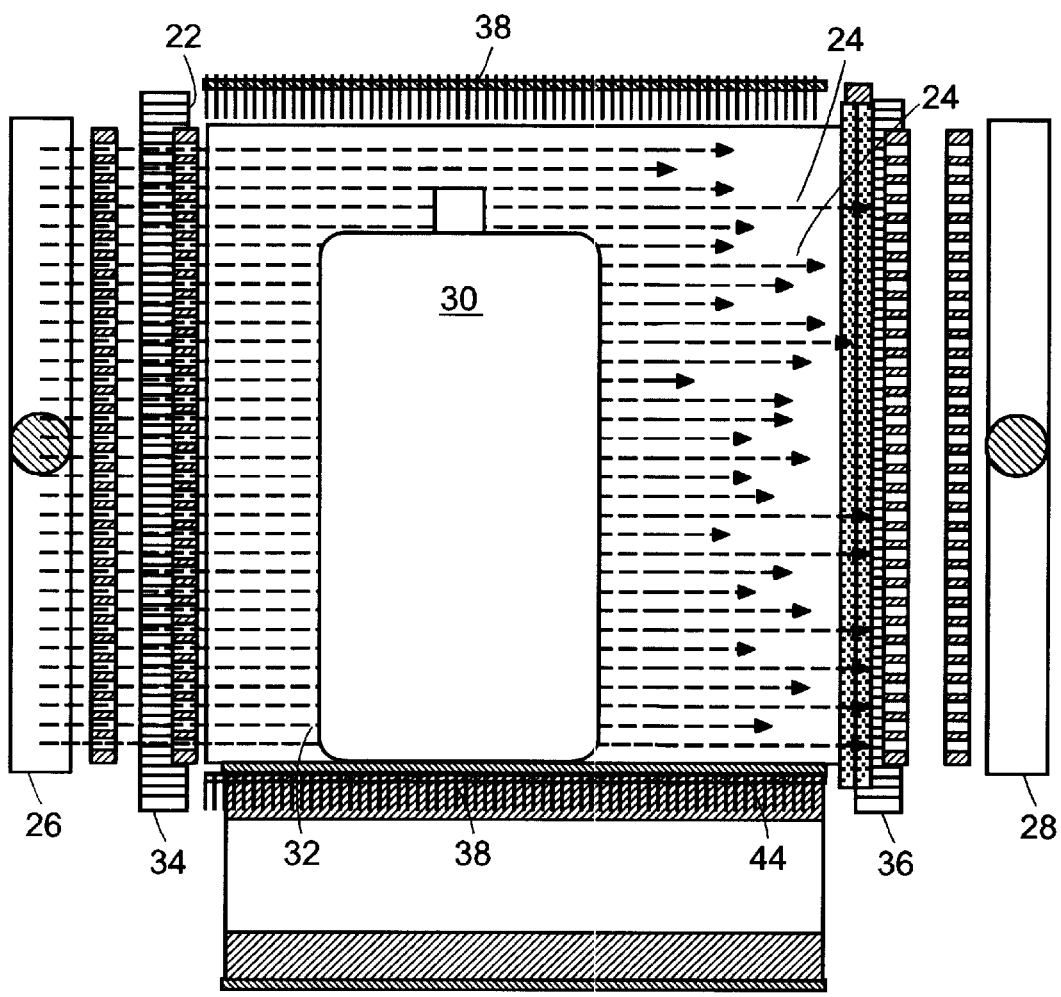
FIG. 2 provides a schematic representation of a source of sequential x-ray beams used in a system to detect concealed objects in luggage using horizontal beams of penetrating radiation.

FIG. 2 shows another preferred embodiment of the present invention wherein penetrating radiation is used in a system for characterizing an object concealed by a concealing surface, for example, a suitcase 30 or a cargo container. In this arrangement, two x-ray sources (26 and 28) are provided to produce sequential beams of radiation 24 that are emitted from collimator 22 parallel to the direction of motion of the container 30. With such an arrangement, the radiation does not pass through the conveyor belt 44. The sequential beams of radiation 24 penetrate concealing surface 32 of container 30. The radiation 24 is scattered by objects within container 30. Back scatter detector 34 is disposed on the same side of container 30 as collimator 22. Transmission detector 36 is disposed on the opposite side of container 30 from collimator 22. Side scatter detectors 38 may be disposed lateral to the collimator 22. Sequential beams of penetrating radiation 24, such as x-rays, may be in the form of a pencil beam that is raster scanned in the plane perpendicular to the beams 24. Detectors 34, 36, and 38 may each include, without limitation, x-ray detectors arranged in a linear or planar configuration.

Figure 3:
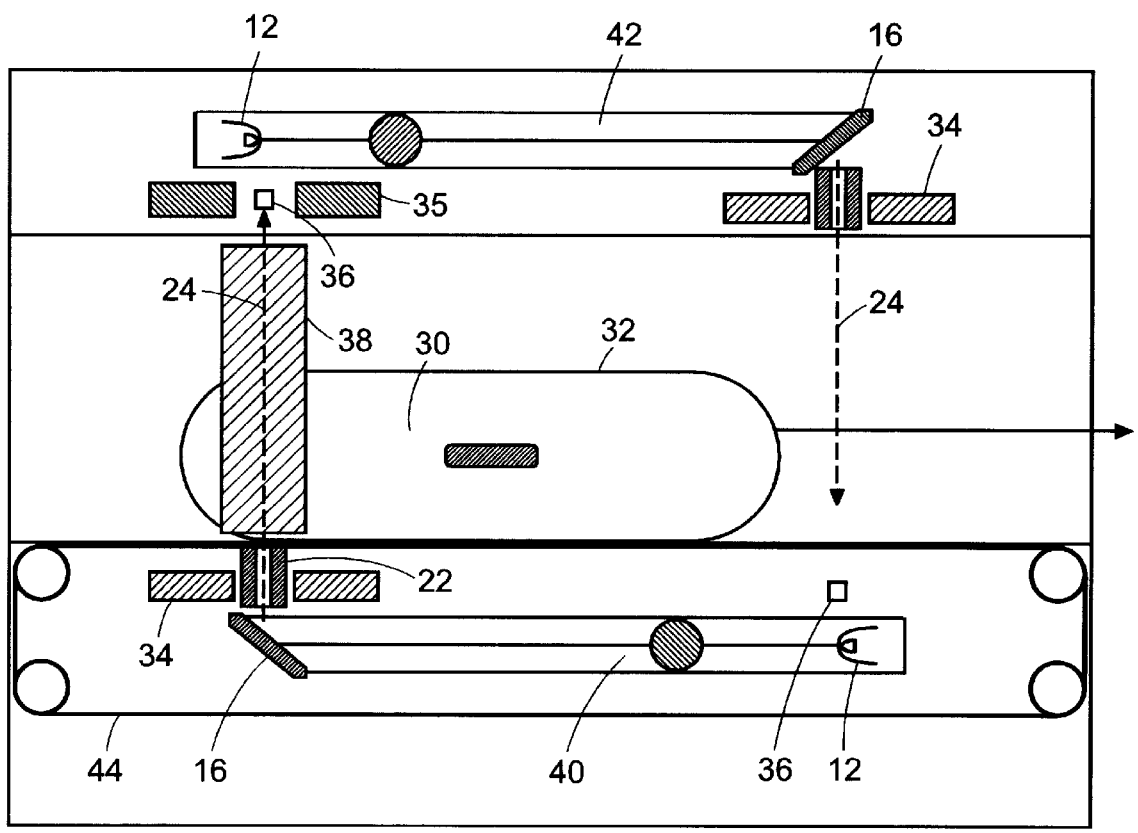
FIG. 3 provides a detailed schematic representation of a preferred embodiment of the present invention in a system to detect concealed objects using sequential penetrating radiation.

FIG. 3 illustrates an inspection system in accordance with another preferred embodiment of the present invention which uses two independent rastered beams of sequential parallel x-rays. One x-ray apparatus 40 sits underneath the container 30 and another x-ray apparatus 42 sits above the container 30. The x-ray apparatuses 40 and 42 are positioned head to toe as shown. The container 30 is moved by a conveyor 44. The lower x-ray apparatus 40, and upper x-ray apparatus 42, may be similar to that shown in FIG. 1. The sequential beams of penetrating radiation 24 are directed perpendicular to the motion of the container 30 on the conveyor belt 44 and move across concealing surface 32 into a transmission detector 36 which detects the x-rays transmitted through container 30. The back scatter detector 34 detects the x-rays that have scattered from the container 30 in the back direction. The detector 35 detects the x-rays that have scattered from container 30 in the forward direction. Detector array 38 detects the x-rays that have scattered from the container 30 sideways. Note that, in general, there will be two detector arrays 38, one on either side of the container 30. Apparatus 42, which sits above the container is shown with only the transmission detector 36 and backscatter detector 34.

It should be noted further that in some applications it may be advantageous to have the x-ray apparatuses, 40 and 42, with their respective detectors, on either side of the container 30, rather than at the top and bottom. Container 30 may be moved along conveyor 44 during inspection by sequential beams of radiation from collimators 22, or may be scanned while stationary. The use of vertical (as in FIG. 3) or horizontal (as in FIG. 2) curtains of radiation is dictated by practical considerations only. For example, the arrangement of FIG. 2 can be simple and inexpensive while the arrangement of FIG. 3 has the advantage of being very compact. The other aspects of the embodiment of FIG. 3 are identical to those described in relation to FIG. 2.

Figure 4:
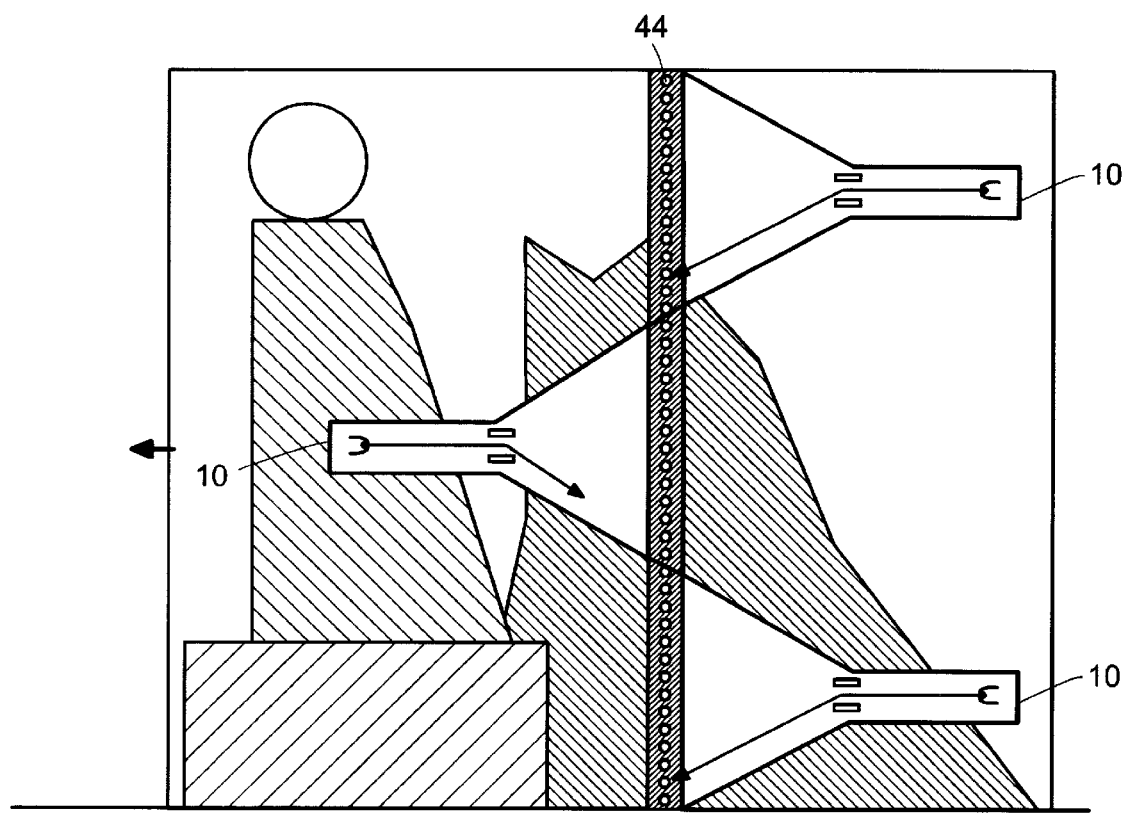
FIG. 4 provides a schematic representation of the embodiment of FIG. 2 as it is used to inspect a very large area.

FIG. 4 shows how the present invention may be used to inspect very large width containers. A plurality of x-ray apparatuses 10, each capable of generating a scanned beam, are displaced along the conveyor 44 either in a row, or otherwise disposed with respect to each other in some manner. It is straightforward to combine a plurality of apparatuses to produce a single image because the images are all produced from parallel and sequential beams of radiation. The use of parallel beams allows the beams to be multiplexed to produce a seamless image.

Figure 5A:
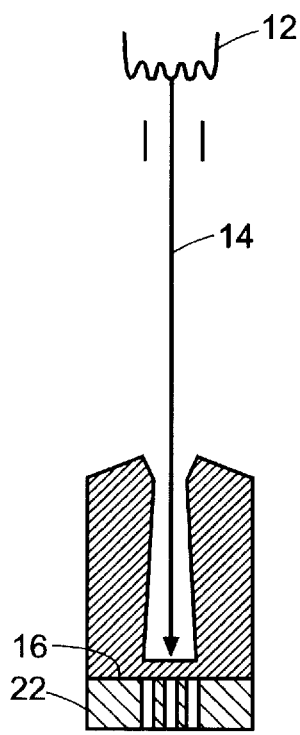
Figure 5B:
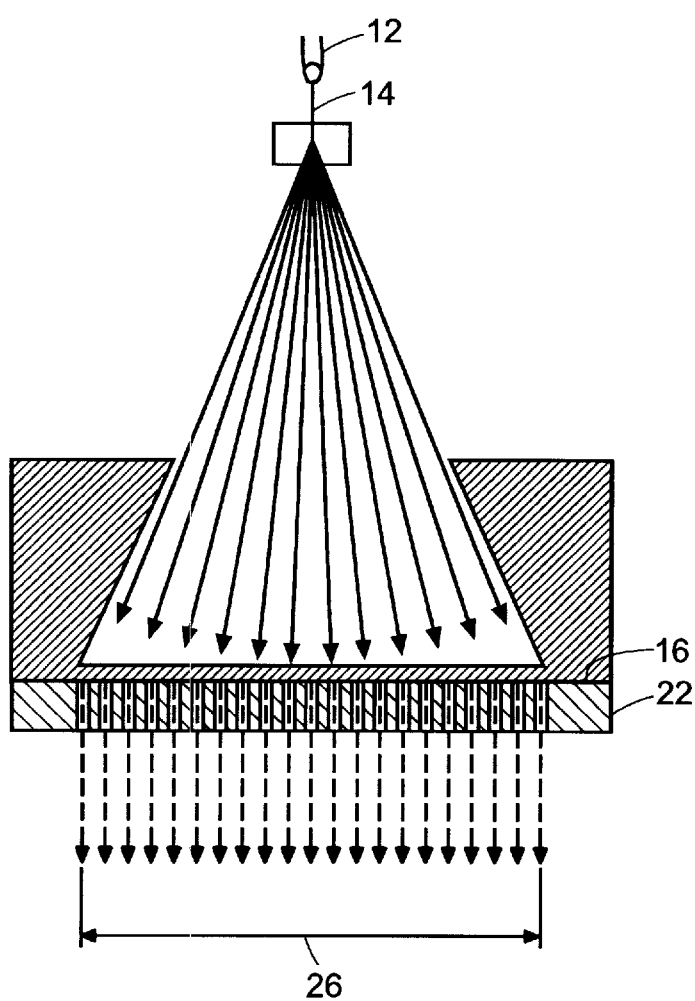
Figure 5C:
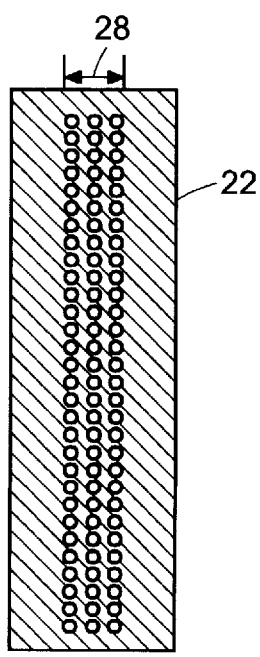

FIGS. 5(a)–5(c) illustrate another preferred embodiment of the invention wherein a two dimensional array of parallel and sequential beams of radiation is produced. As shown in FIG. 5(a) a single beam of charged particles 14 impinges upon a target 16. The beam 14 is scanned over the target as shown in FIG. 5(b). The single beam of particles 14 creates a two dimensional array of parallel and sequential beams of radiation due to the configuration of the collimator 22 which is shown more clearly in FIG. 5(c). The range of scanning defines a defining area of scanning, that is, the product of the dimension 26 by the dimension 28 in the orthogonal direction. In addition to scanning, the beam of particles 14 may readily be directed to particular positions or regions, such as when additional scrutiny of an area of an object is called for.

Figure 6A:
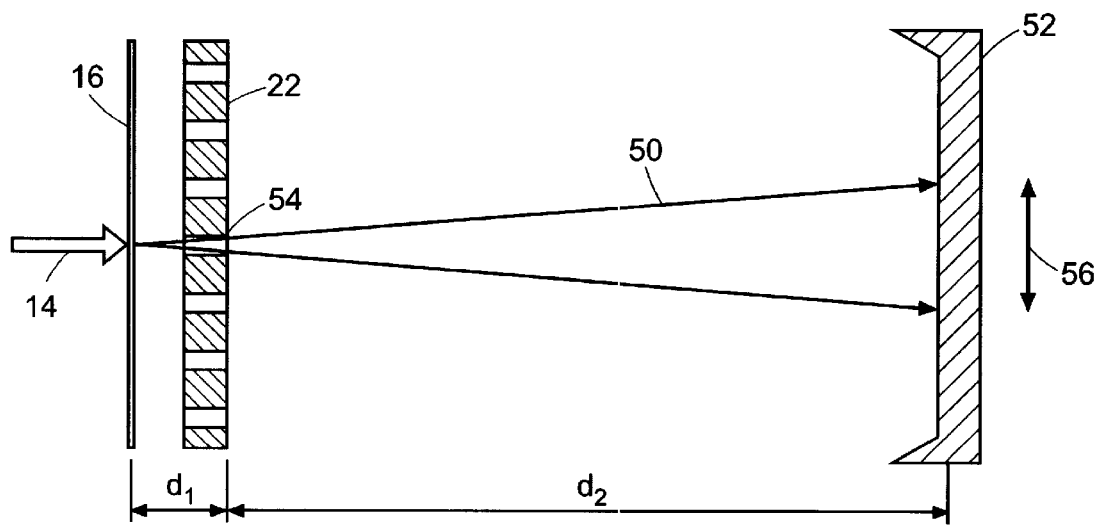
FIGS. 6(a) and 6(b) provide a schematic representation of a preferred embodiment of the present invention wherein the spatial resolution of an imaging system is achieved.
Figure 6B:
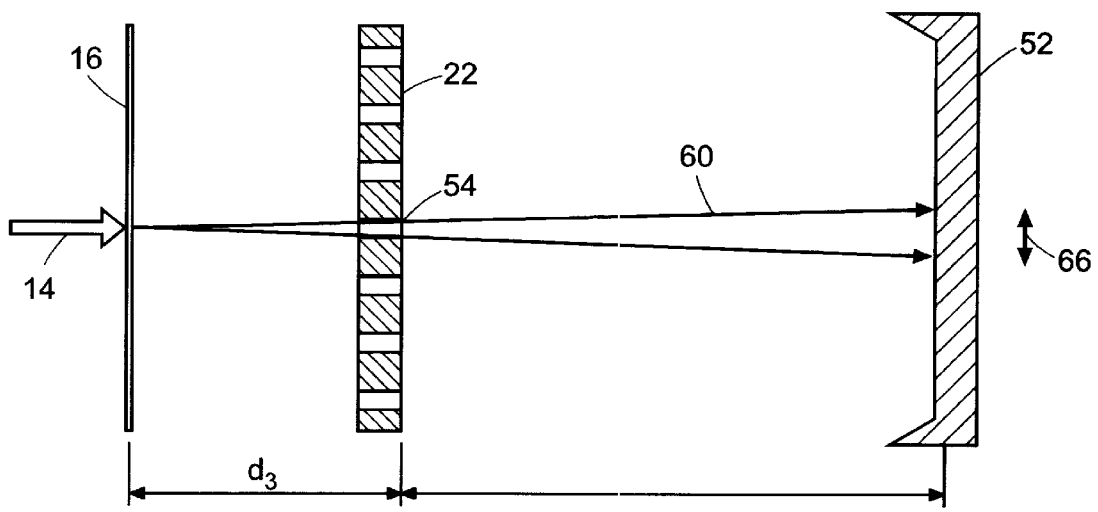

FIGS. 6(a) and 6(b) illustrate how a source of electromagnetic radiation of variable beam opening can be produced by varying the distance of the collimator-array plane with respect to the x-ray generating plane and, at the same time, reducing the dimensions that the particle beam scans of the target. In this way, specific areas of the container can be examined with better resolution than is practical with a scan over the full area of the container. For purposes of this disclosure "beam opening" is defined as the half angle of the cone of radiation emitted from one aperture of the collimator array.

As can be seen in FIG. 6(a), the size of the beam opening 50 increases with its distance from the target 16. In FIG. 6(a), the collimator 22 is a distance d1 from the target 16, and a distance d2 from the detector 52. The size of the beam opening 50 at the detector 52 is the radius of the collimator aperture 54 times the ratio (d1+d2)/d1. As the aperture 54 is moved further form the target 16, the size of the beam opening 50 decreases. In FIG. 6(b), the distance d3 is three times that of distance d1 and the angular spread of the beam 60 is three times smaller than the angular spread of the beam 50. Thus, the resolution 66 is three times higher than the resolution 56. The raster scanning technique of this invention allows the operator to select the area of the scan as well as the dwell time per pixel so as to attain the best spatial resolution and image contrast of a given object.

Figure 7:
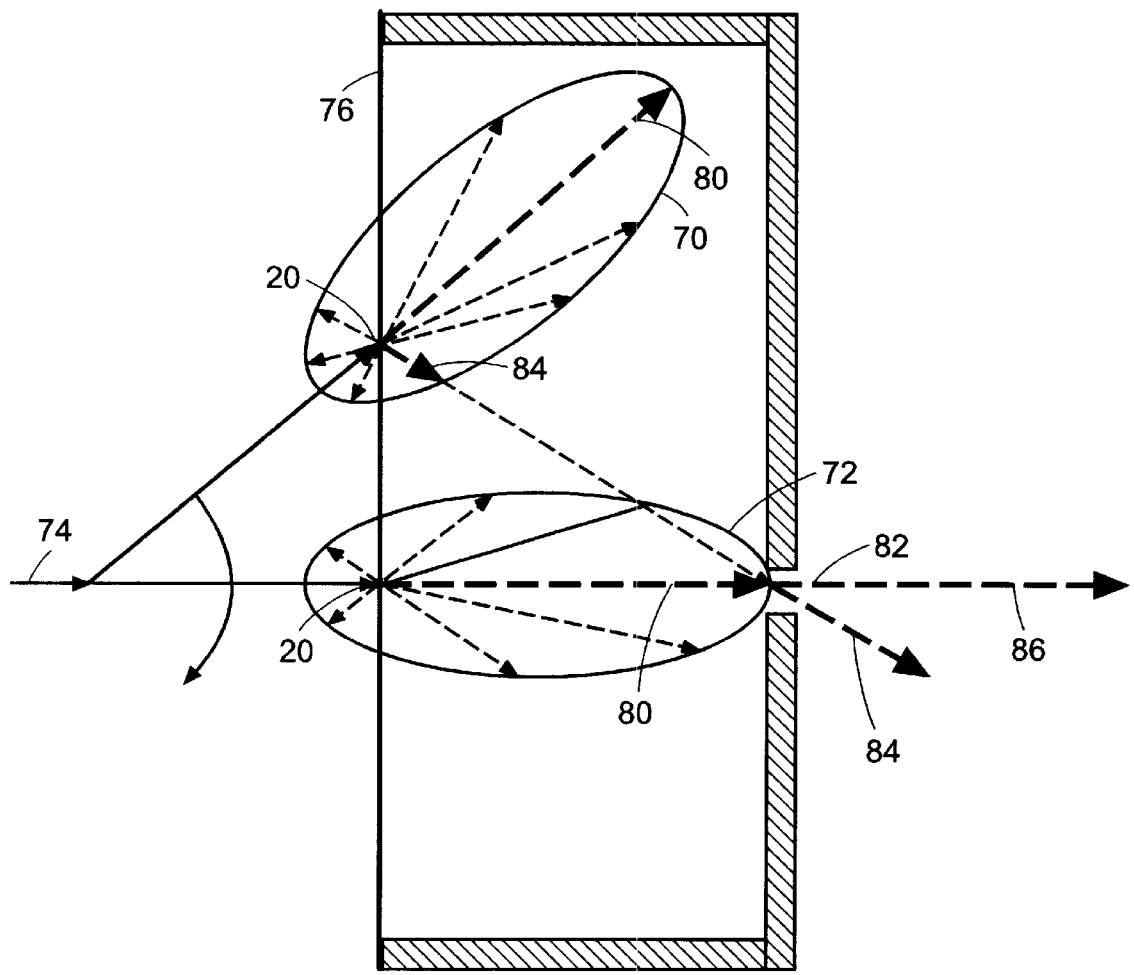
FIG. 7 provides a schematic representation illustrating the non-uniformity of x-ray beams which are generated by a high energy scanned electron beam.

FIG. 7 illustrates how non-uniform x-ray beams 70 and 72 are generated when high energy particles impinge upon a target in prior art systems. A high energy electron beam 74 is deflected toward an anode 76 by a steering magnet 78. The electron beam 74 may strike the anode 76 either head on 72 or at an angle 70. The x-ray radiation pattern is shown as an ellipse with the greatest intensity in the direction of the electron 80 and the least intensity in the back direction. If one uses a pin-hole collimator 82 to select an emergent x-ray, then the x-ray intensities and energy spectra through the pin-hole are very different in the cases as shown by components 84 and 86.

FIG. 8 shows a preferred embodiment of the present invention which obviates the problem illustrated by FIG. 7. A beam of charged particles 14 is directed by a electromagnetic beam director 90. The particles 14 then pass through a electromagnetic steering device 92, which may be the field of an electromagnet or permanent magnet, and emerge in beams 94 that are parallel to the original direction of the particle beam 14. Electromagnetic steering means for producing the beams of electrons that are parallel to, but displaced from, the originating beam are well known in the art. The parallel beams 94 hit the target 16 at a substantially ninety degree angle to the target. The forward component of the uniform radiation 96 traverses a collimator 22 with parallel transmitting regions 98 to produce high energy parallel beams of radiation 100. Transmitting regions 98 may be apertures, for example, or rods or hollow tubes of a material, such as plastic, that attenuates the x-rays substantially less than the surrounding attenuating material.

Advantages of preferred embodiments of the present invention include electromagnetic control of the region over which the particles scan the target and, consequently, control of the region over which the penetrating electromagnetic radiation scans the area to be inspected. Additionally, the invention provides electromagnetic control of the penetrating radiation beam at every point so that intensity and dwell time can be modulated for different purposes. For example, the time to inspect a large object can be minimized by changing the dwell time in each pixel according to the amount of absorption suffered by the penetrating radiation beam. This is particularly advantageous in the case of a moving vehicle. Further, ambient radiation can by minimized by modulating the radiation intensity so that minimal radiation is emitted in directions where the safety of persons might be jeopardized.

Another particularly strong advantage of the approach of the present invention is that higher beam currents may be attained for the same focal spot size. Mechanical scanning systems use x-ray tubes in which the electron beam trajectory is fixed. If the anode is stationary, then the maximum electron power that can be sustained is determined by the ability of the anode to carry away heat, and that ability is a direct function of beam power in the focal spot. Since the focal spot is a primary determinant of the best attainable spatial resolution, it is important to keep its dimensions small. At the same time, one would like to generate the maximum number of x-rays, which requires the maximum power. If the electron beam spot on the anode is stationary, as it is in the standard x-ray tube, then the designer must strike a compromise between beam flux and beam resolution. To increase the effective area, keeping the beam spot sized fixed, rotating anode tubes are available; the effective target area is just the circumference of the rotating circle times the perpendicular length of the electron beam on the anode. In the approach of the present invention, however, the effective cooling area is the effective focal spot diameter times the length of the scan, which can be much greater than the circumferential length of a rotating anode tube. Calculations show that, with the present invention, the power density in the particle beam can be as much as one hundred times greater than can be used with commercial x-ray tubes using fixed electron beams and thus the effective spatial resolution can be more than ten times smaller.

In addition, use of sequential and parallel beams of radiation may advantageously provide an undistorted image and minimize the distortion due to the scan position. Further, sequential and parallel beams of radiation make the intensity of the radiation more uniform for a given energy of the charged particles used to generate the radiation.

Other advantages of the present invention include reduction of the footprint of xray inspection systems, greater flexibility in the geometrical design of detectors, and creation of a seamless image of a large area by combining independent images of portions of the area.

Finally, the electromagnetic scanning method of the present invention has the potential for easily producing true zooming because a change in the position of the collimator array relative to the emitting target changes the resolution.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A system for inspecting the contents of a container, the system comprising:
   a first apparatus for emitting sequential beams of penetrating electromagnetic radiation from a target in a first set of substantially parallel directions; the first apparatus including:
      a source for producing a beam of charged particles,
      a target having a surface which receives the beam of charged particles and emits electromagnetic waves in response thereto,
      an electromagnetic beam director that directs the beam of charged particles to a plurality of specified locations on the target,
      an electromagnetic steering device disposed proximal to the target, the electromagnetic steering device directing the charged particles to strike the target at a substantially ninety degree angle to the surface of the target, and
      a collimator, the collimator having an array of transmitting regions and being disposed proximal to the target such that electromagnetic wave emitted from the target pass through the collimator and emerge from the array of transmitting regions in a series of parallel beams;
   a conveyor for moving the container relative to the first source;
   a first detector for detecting the penetrating radiation after interaction with the contents of the container and generating a first set of signals corresponding to each of the substantially parallel directions; and
   a controller for characterizing the contents of the container based at least on the first set of signals.

2. A system according to claim 1, wherein the first detector is a scatter detector.

3. A system according to claim 1, wherein the first detector is a transmission detector.

4. A system according to claim 1, further comprising:
   a second apparatus for emitting penetrating electromagnetic radiation directed in a direction substantially opposite to the first set of substantially parallel directions.

5. A system according to claim 4, further comprising:
   a second detector for detecting radiation after interaction with the contents of the container and generating a second signal corresponding to the substantially opposite direction.

6. A system according to claim 5, wherein the second detector is a scatter detector.

7. A system according to claim 5, wherein the second detector is a transmission detector.

8. A system according to claim 4, wherein the second apparatus for emitting penetrating electromagnetic radiation comprises:
   a source for producing a beam of charged particles;
   a target having a surface which receives the beam of charged particles and emits electromagnetic waves in response thereto;
   an electromagnetic beam director that directs the beam of charged particles to a plurality of specified locations on the target;
   an electromagnetic steering device disposed proximal to the target, the electromagnetic steering device directing the charged particles to strike the target at a substantially ninety degree angle to the surface of the target; and
   a collimator, the collimator having an array of transmitting regions and being disposed proximal to the target such that electromagnetic wave emitted from the target pass through the collimator and emerge from the array of transmitting regions in a series of parallel beams.

9. A system according to claim 8, further comprising:
   a second detector for detecting radiation after interaction with the contents of the container and generating a second signal corresponding to the substantially opposite direction.

10. A system according to claim 9, wherein the second detector is a scatter detector.

11. A system according to claim 9, wherein the second detector is a transmission detector.

* * * * *